US006391608B1

(12) United States Patent
Kong et al.

(10) Patent No.: US 6,391,608 B1
(45) Date of Patent: May 21, 2002

(54) **METHOD FOR CLONING AND EXPRESSION OF *PLEI* RESTRICTION ENDONUCLEASE AND PLEI AND BSTNBII METHYLASES IN *E. COLI***

(75) Inventors: Huimin Kong, Wenham; Lauren Sears Higgins, Essex, both of MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/813,872

(22) Filed: Mar. 21, 2001

(51) Int. Cl.$^7$ .................................................. C12N 9/22
(52) U.S. Cl. ................ 435/199; 435/252.3; 435/320.1; 536/23.2
(58) Field of Search ........................... 435/320.1, 252.3, 435/199; 536/23.2

(56) References Cited

U.S. PATENT DOCUMENTS

| | | | |
|---|---|---|---|
| 5,200,333 A | 4/1993 | Willson | 435/172.3 |
| 5,498,535 A | 3/1996 | Fomenkov et al. | 435/172.3 |
| 6,191,267 B1 * | 2/2001 | Kong et al. | 536/23.4 |

OTHER PUBLICATIONS

Higgins, L.S, et al. (2001) Nucl. Acids Res. 29(12), 2492–2501.*
Blumenthal, et al., J. Bacteriol. 164:501–509 (1985).
Bougueleret, et al., Nucl. Acids Res. 12:3659–3676 (1984).
Theriault and Roy, Gene 19:355–359 (1982).
Fomenkov, et al., Nucl. Acids Res. 22:2399–2403 (1994).
Gingeras and Brooks, Proc. Natl. Acad. Sci. 80:402–406 (1983).
Janulaitis, et al., Gene 20:197–204 (1982).
Kiss, et al., Nucl. Acids Res. 13:6403–6421 (1985).
Kiss and Baldauf, Gene 21:111–119 (1983).
Kosykh, et al., Mol. Gen. Genet. 178:717–718 (1980).
Malone, et al., J. Mol. Biol. 253:618–632 (1995).
Mann, et al., Gene 3:97–112 (1978).
New England Biolabs' catalog 2000–2001, p. 220.
Roberts, et al., Nucl. Acids Res. 27:312–313 (1999).
Szomolanyi, et al., Gene 10:219–225 (1980).
Walder, et al. J. Biol. Chem. 258:1235–1241 (1983).
Walder, et al., Proc. Natl. Acad. Sci. USA 78:1503–1507 (1981).
Wayne, et al., Gene 202–83–88 (1997).

* cited by examiner

*Primary Examiner*—Charles L. Patterson, Jr.
(74) *Attorney, Agent, or Firm*—Gregory D. Williams (57) ABSTRACT

The present invention relates to recombinant DNA which encodes the PleI restriction endonuclease as well as PleI and BstNBII methyltransferase and expression of PleI restriction endonuclease and M.BstNBII in *E. coli* cells containing the recombinant DNA.

5 Claims, 6 Drawing Sheets

Figure 1

R: restriction endonuclease gene, pleIR
M: modification methylase gene, pleIM

Figure 2-1

```
              10                      30                       50
ATGAAGCCATTAGTTAAATATAGAGGTGGAAAGTCTAAGGAAATTCCATATCTAATTAAA
MetLysProLeuValLysTyrArgGlyGlyLysSerLysGluIleProTyrLeuIleLys 70                      90                      110
CATATCCCTGAATTTAAAGGGCGCTACATAGAGCCTTTTTTTGGTGGGGGGCTTTATTT
HisIleProGluPheLysGlyArgTyrIleGluProPhePheGlyGlyGlyAlaLeuPhe 130                     150                      170
TTTTATATAGAGCCAGAAAAATCTATTATCAATGACATTAATAAAAAACTTATAGATTTT
PheTyrIleGluProGluLysSerIleIleAsnAspIleAsnLysLysLeuIleAspPhe 190                     210                      230
TATCGAGATGTTAAAGATAACTTTGTTCAATTGCGTCATGAGCTTGATGAGATAGAATGT
TyrArgAspValLysAspAsnPheValGlnLeuArgHisGluLeuAspGluIleGluCys 250                     270                      290
ATTTATGAAAAGAATAGAGTTGAATACGAAACTAGAAAGAAATTAAATCCTACTGAACGT
IleTyrGluLysAsnArgValGluTyrGluThrArgLysLysLeuAsnProThrGluArg 310                     330                      350
GTAGATGATGGAAATGAAGATTTCTATTACTTCATGAGGAATGAATTCAATAAAGATTTT
ValAspAspGlyAsnGluAspPheTyrTyrPheMetArgAsnGluPheAsnLysAspPhe 370                     390                      410
TCGGATAGATATCTTTCATCAACACTGTATTTTTATATAAATAAGACTGCGTACTCTGGA
SerAspArgTyrLeuSerSerThrLeuTyrPheTyrIleAsnLysThrAlaTyrSerGly 430                     450                      470
ATGATTAGATATAACTCAAAAGGTGAGTTTAATGTTCCGTTTGGTAGATATAAAAATCTC
MetIleArgTyrAsnSerLysGlyGluPheAsnValProPheGlyArgTyrLysAsnLeu 490                     510                      530
AATACAAAACTTGTGGCTAATGAACATCACTTGTTAATGCAGGGTGCTCAGATATTTAAT
AsnThrLysLeuValAlaAsnGluHisHisLeuLeuMetGlnGlyAlaGlnIlePheAsn 550                     570                      590
GAAGATTACAGCGAGATCTTCAAGATGGCGAGAAAAGATGATTTTATATTTCTAGACCCT
GluAspTyrSerGluIlePheLysMetAlaArgLysAspAspPheIlePheLeuAspPro 610                     630                      650
CCCTATGATTGCGTATTTAGTGATTATGGTAATGAGGAATATAAAGATGGTTTCAATGTA
ProTyrAspCysValPheSerAspTyrGlyAsnGluGluTyrLysAspGlyPheAsnVal 670                     690                      710
GATGCTCATGTGAAATTGAGTGAGGACTTTAAGAAATTGAAATGCAAAGCCATGATGGTT
AspAlaHisValLysLeuSerGluAspPheLysLysLeuLysCysLysAlaMetMetVal
```

Figure 2-2

```
          730                     750                     770
ATCGGTAAGACTGAATTGACTGATGGGTTGTATAAGAAAATGATTATTGATGAATACGAT
IleGlyLysThrGluLeuThrAspGlyLeuTyrLysLysMetIleIleAspGluTyrAsp 790                     810                     830
AAAAGTTATTCTGTGAATATAAGGAATAGATTTAAGTCTGTTGCAAAGCATATAGTTGTT
LysSerTyrSerValAsnIleArgAsnArgPheLysSerValAlaLysHisIleValVal

850
GCAAATTATTGA
AlaAsnTyrEnd
```

Figure 3-1

```
              10                      30                      50
ATGGCAAAGCCTATTGATAGTAAAGTTCTATTTATTACTACGTCACCACGAACGCCTGAA
MetAlaLysProIleAspSerLysValLeuPheIleThrThrSerProArgThrProGlu 70                      90                     110
AAGATGGTTCCTGAGATAGAGCTTTTAGATAAGAATTTTAATGGGGATGTTTGGAATAAA
LysMetValProGluIleGluLeuLeuAspLysAsnPheAsnGlyAspValTrpAsnLys 130                     150                     170
GATACCCAAACTGCATTCATGAAAATTCTTAAAGAAGAAAGTTTCTTTGATGGTGAAGGT
AspThrGlnThrAlaPheMetLysIleLeuLysGluGluSerPhePheAspGlyGluGly 190                     210                     230
AAGAATGATCCTGCATTTAGTGCTAGAGATAGAATAAATAGAGCGCCAAAATCACTAGGT
LysAsnAspProAlaPheSerAlaArgAspArgIleAsnArgAlaProLysSerLeuGly 250                     270                     290
TTTGTCATTTTGACACCTAAATTATCTTTAACTGATGCTGGTGTTGAGTTAATTAAAGCA
PheValIleLeuThrProLysLeuSerLeuThrAspAlaGlyValGluLeuIleLysAla 310                     330                     350
AAAAGAAAAGATGATATATTTTTGAGGCAAATGCTTAAATTTCAGCTGCCATCTCCATAC
LysArgLysAspAspIlePheLeuArgGlnMetLeuLysPheGlnLeuProSerProTyr 370                     390                     410
CATAAGTTATCAGATAAGGCAGCACTTTTTTATGTAAAACCTTATCTTGAAATATTTAGA
HisLysLeuSerAspLysAlaAlaLeuPheTyrValLysProTyrLeuGluIlePheArg 430                     450                     470
TTGGTTCGTCATTTTGGTTCTTTGACCTTTGATGAGTTAATGATTTTTGGTTTGCAAATT
LeuValArgHisPheGlySerLeuThrPheAspGluLeuMetIlePheGlyLeuGlnIle 490                     510                     530
ATAGATTTTAGAATTTTTAATCAAATTGTTGATAAAATTGAAGATTTTAGAGTGGGTAAG
IleAspPheArgIlePheAsnGlnIleValAspLysIleGluAspPheArgValGlyLys 550                     570                     590
ATTGAAAATAAAGGTAGGTATAAAACTTATAAAAAGAGCGGTTTGAGGAAGAGCTTGGG
IleGluAsnLysGlyArgTyrLysThrTyrLysLysGluArgPheGluGluGluLeuGly 610                     630                     650
AAAATATATAAAGATGAGTTGTTTGGTTTAACAGAGGCTTCGGCTAAAACGTTAATTACC
LysIleTyrLysAspGluLeuPheGlyLeuThrGluAlaSerAlaLysThrLeuIleThr 670                     690                     710
AAAAAAGGTAACAATATGAGGGACTATGCTGATGCATGCGTTAGATATTTGCGTGCGACA
LysLysGlyAsnAsnMetArgAspTyrAlaAspAlaCysValArgTyrLeuArgAlaThr
```

Figure 3-2

```
            730                  750                  770
GGGATGGTTAATGTTTCTTATCAAGGGAAATCTCTCTCAATTGTTCAAGAGAAAAAAGAA
GlyMetValAsnValSerTyrGlnGlyLysSerLeuSerIleValGlnGluLysLysGlu 790                  810                  830
GAAGTTGATTTCTTTTTAAAGAATACTGAGAGAGAACCTTGCTTTATAAATGATGAAGCA
GluValAspPhePheLeuLysAsnThrGluArgGluProCysPheIleAsnAspGluAla 850                  870                  890
TCATATGTGAGTTATCTTGGTAATCCTAATTACCCCAAACTTTTTGTTGATGACGTAGAT
SerTyrValSerTyrLeuGlyAsnProAsnTyrProLysLeuPheValAspAspValAsp 910                  930                  950
AGGATTAAAAAGAAACTTCGATTTGATTTTAAGAAGACTAATAAAGTTAATGCCTTGACA
ArgIleLysLysLysLeuArgPheAspPheLysLysThrAsnLysValAsnAlaLeuThr 970                  990                 1010
CTTCCTGAGTTGAAAGAGGAGTTAGAGAATGAAATTCTAAGTAGAAAAGAGAATATATTA
LeuProGluLeuLysGluGluLeuGluAsnGluIleLeuSerArgLysGluAsnIleLeu 1030                 1050                 1070
AAAAGTCAAATATCTGATATTAAAAACTTTAAGTTATACGAAGACATTCAAGAGGTTTTT
LysSerGlnIleSerAspIleLysAsnPheLysLeuTyrGluAspIleGlnGluValPhe 1090                 1110                 1130
GAGAAGATAGAAAATGATAGAACACTATCTGATGCTCCATTGATGCTTGAATGGAATACA
GluLysIleGluAsnAspArgThrLeuSerAspAlaProLeuMetLeuGluTrpAsnThr 1150                 1170                 1190
TGGCGTGCAATGACTATGCTGGATGGTGGTGAAATCAAAGCAAATTTGAAATTTGATGAT
TrpArgAlaMetThrMetLeuAspGlyGlyGluIleLysAlaAsnLeuLysPheAspAsp 1210                 1230                 1250
TTTGGAAGTCCAATGTCTACGGCTATTGGAAATATGCCAGATATAGTGTGTGAATATGAT
PheGlySerProMetSerThrAlaIleGlyAsnMetProAspIleValCysGluTyrAsp 1270                 1290                 1310
GACTTCCAGTTGTCTGTAGAAGTCACAATGGCAAGCGGGCAAAAGCAATATGAAATGGAA
AspPheGlnLeuSerValGluValThrMetAlaSerGlyGlnLysGlnTyrGluMetGlu 1330                 1350                 1370
GGTGAGCCAGTCTCGCGGCACTTAGGTAAACTAAAGAAAAGTTCTGAAAAACCAGTATAT
GlyGluProValSerArgHisLeuGlyLysLeuLysLysSerSerGluLysProValTyr 1390                 1410                 1430
TGTTTATTCATTGCTCCTAAAATTAATCCATCCTCAGTAGCACACTTCTTTATGTCTCAT
CysLeuPheIleAlaProLysIleAsnProSerSerValAlaHisPhePheMetSerHis 1450                 1470                 1490
AAAGTGGATATTGAATATTATGGTGGGAAAAGCCTAATTATTCCTTTGGAGTTAAGTGTT
LysValAspIleGluTyrTyrGlyGlyLysSerLeuIleIleProLeuGluLeuSerVal
```

Figure 3-3

```
         1510                1530                1550
TTTAGGAAGATGATTGAGGATACTTTTAAAGCATCGTATATACCAAAATCTGATAATGTT
PheArgLysMetIleGluAspThrPheLysAlaSerTyrIleProLysSerAspAsnVal 1570                1590                1610
CATAAATTATTTAAGAATTTTGCTTCAATTGCAGATGAGGCAGGTAATGAGAAAGTTTGG
HisLysLeuPheLysAsnPheAlaSerIleAlaAspGluAlaGlyAsnGluLysValTrp 1630                1650                1668
TATGAAGGTGTAAAAAGAACTGCAATGAATTGGCTTTCTTTAAGCTAA
TyrGluGlyValLysArgThrAlaMetAsnTrpLeuSerLeuSerEnd
```

METHOD FOR CLONING AND EXPRESSION OF *PLEI* RESTRICTION ENDONUCLEASE AND PLEI AND BSTNBII METHYLASES IN *E. COLI*

BACKGROUND OF THE INVENTION

The present invention relates to recombinant DNA which encodes the PleI restriction endonuclease (endonuclease) as well as the PleI methyltransferase and the BstNBII methyltransferase (methylase). The present invention also relates to the expression of PleI restriction endonuclease and BstNBII methylase in *E. coli* cells containing the recombinant DNA.

PleI endonuclease and methyltransferase are found in the strain of *Pseudomonas lemoignei* (New England Biolabs' strain collection #418). The endonuclease (R.PleI) recognizes the double-stranded DNA sequence 5'GAGTC 3' and cleaves DNA 4 and 5 bases downstream generating a one-base 5' overhanging end. The PleI methyltransferase (M.PleI) recognizes the double-stranded DNA sequence 5'GASTC 3' and modifies the N6-adenine by addition of a methyl group to become N6-methyladenine in the DNA sequence.

BstNBII methylase (M.BstNBI) is found in the strain of *Bacillus stearothermophilus* 33M (New England Biolabs' strain collection #928). It recognizes the double-stranded DNA sequence 5'GASTC 3' and modifies the N6-adenine by addition of a methyl group to become N6-methyladenine in the DNA sequence. PleI/BstNBII sites that are N6mA modified by M.BstNBII are resistant to both BstNBII and PleI restriction.

Type II and type IIs restriction endonucleases are classes of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along the DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313, (1999)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3', 5'PuG/GNCCPy3' and 5'CACNNN/GTG3' respectively. *Escherichia coli* RY13, on the other hand, produces only one enzyme, EcoRI, which recognizes the sequence 5'G/AATTC3'.

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II and a few type IIs restriction-modification systems have been cloned. The first cloning method used bacteriophage infection as a means of identifying or selecting restriction endonuclease clones (EcoRII: Kosykh et al., Mol. Gen. Genet. 178:717–719, (1980); HhaII: Mann et al., Gene 3:97–112, (1978); PstI: Walder et al., Proc. Nat. Acad. Sci. 78:1503–1507, (1981)). Since the expression of restriction-modification systems in bacteria enable them to resist infection by bacteriophage, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., Nucl. Acids. Res. 12:3659–3676, (1984); PaeR7: Gingeras and Brooks, Proc. Natl. Acad. Sci. USA 80:402–406, (1983); Theriault and Roy, Gene 19:355–359 (1982); PvuII: Blumenthal et al., J. Bacteriol. 164:501–509, (1985); Tsp45I: Wayne et al. Gene 202:83–88, (1997)).

A third approach is to select for active expression of methylase genes (methylase selection) (U.S. Pat. No. 5,200,333 and BsuRI: Kiss et al., Nucl. Acids. Res. 13:6403–6421 (1985)). Since restriction-modification genes are often closely linked together, both genes can often be cloned simultaneously. This selection does not always yield a complete restriction system however, but instead yields only the methylase gene (BspRI: Szomolanyi et al., Gene 10:219–225 (1980); BcnI: Janulaitis et al., Gene 20:197–204 (1982); BsuRI: Kiss and Baldauf, Gene 21:111–119 (1983); and MspI: Walder et al., J. Biol. Chem. 258:1235–1241 (1983)).

A more recent method, the "endo-blue method", has been described for direct cloning of thermostable restriction endonuclease genes into *E. coli* based on the indicator strain of *E. coli* containing the dinD::lacZ fusion (Fomenkov et al., U.S. Pat. No. 5,498,525; Fomenkov et al., Nucl. Acids Res. 22:2399–2403, (1994)). This method utilizes the *E. coli* SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that sometimes positive blue clones containing a restriction endonuclease gene are difficult to culture due to the lack of the cognate methylase gene.

There are three major groups of DNA methyltransferases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632, (1995)). When a restriction site on DNA is modified (methylated) by the methylase, it is resistant to digestion by the cognate restriction endonuclease. Sometimes methylation by a non-cognate methylase can also confer the DNA site resistant to restriction digestion. For example, Dcm methylase modification of 5'CCWGG3' (W=A or T) can also make the DNA resistant to PspGI restriction digestion. Another example is that CpM methylase can modify the CG dinucloetide and make the NotI site (5'GCGGCCGC3') refractory to NotI digestion (New England Biolabs' catalog, 2000-01, page 220). Therefore methylases can be used as a tool to modify certain DNA sequences and make them uncleavable by restriction enzymes.

Because purified restriction endonucleases and modification methylases are useful tools for creating recombinant molecules in the laboratory, there is a strong commercial interest to obtain bacterial strains through recombinant DNA techniques that produce large quantities of restriction enzymes. Such over-expression strains should also simplify the task of enzyme purification.

SUMMARY OF THE INVENTION

The present invention relates to a method for cloning the PleI restriction endonuclease from *Pseudomonas lemoignei* into *E. coli* by methylase selection and inverse PCR amplification of the adjacent DNA. A methylase gene with high homology to amino-methyltransferases (N6-adenine methylases) was found in the *Pseudomonas lemoignei* DNA library after methylase selection. This gene was named PleI methylase gene (pleIM).

In order to clone the PleI endonuclease gene in a large DNA fragment, partial ApoI genomic DNA fragment libraries were constructed using the pUC19 vector. Methylase positive clones were obtained. However, no endonuclease activity was detected in any of the M.PleI positive clones.

Since methylase selection failed to yield a PleI endonuclease clone, inverse PCR was employed to amplify the adjacent downstream DNA sequence. An open reading frame was found adjacent to the pleIM gene. This ORF was named pleIr and was expressed along with pleIM in the pUC19 vector. The amount of PleI produced by this clone was virtually undetectable.

To overexpress the pleIM gene, the gene was amplified by PCR and cloned into expression vectors pUC19, pNEB193 and pUC19. None of these constructs conferred 100% resistance to PleI digestion and were therefore not useful for overexpression of the PleI endonuclease.

Methylase selection on the *Bacillus stearothermophilus* 33M genomic DNA had yielded a N6-adenine methylase that conferred protection against PleI digestion when expressed in the pSXY20 plasmid. This construct was used in conjunction with a pleIR-pAGR3 plasmid in *E.coli* strain ER2502 and overexpression of pleIR was achieved. Approximately 100,000 units were produced per gram cells.

BRIEF DESCRIPTION OF THE DRAWINGS

FIG. 2. DNA sequence of PleI methylase gene (pleIM, 957 bp) (SEQ ID NO:1) and its encoded amino acid sequence (SEQ ID NO:2).

FIG. 3. DNA sequence of PleI endonuclease gene (pleIR, 864 bp) (SEQ ID NO:3) and its encoded amino acid sequence (SEQ ID NO:4).

DETAILED DESCRIPTION OF THE INVENTION

Figure 1:
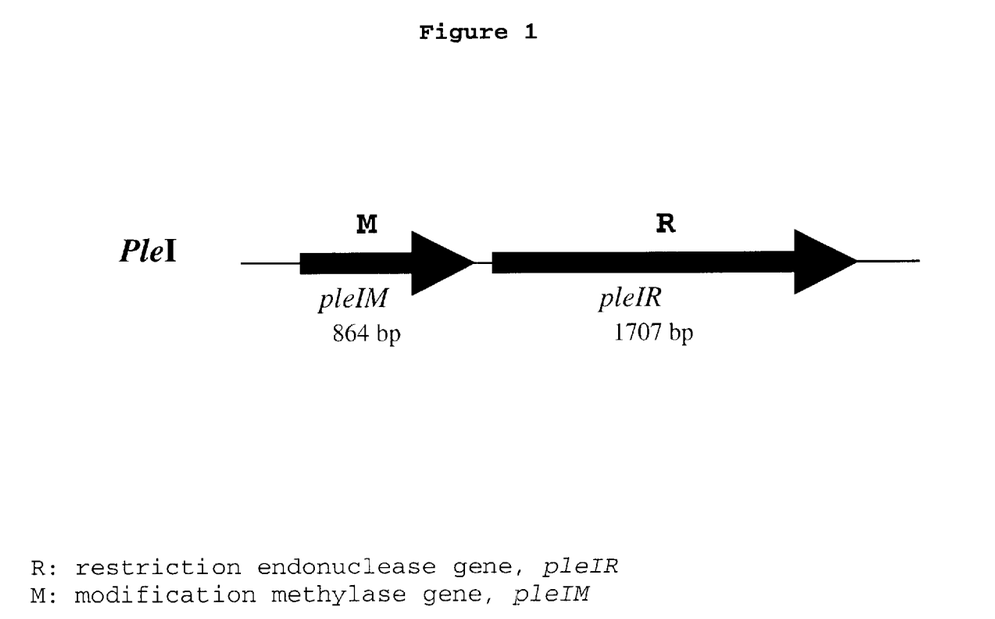
FIG. 1. Gene organization of PleI restriction-modification system. pleIR, PleI restriction endonuclease gene; pleIM, PleI methylase gene.

The method described herein by which the PleI methylase gene, the PleI restriction endonuclease gene and the BstNBII methylase gene are preferably cloned and expressed in *E. coli* using the following steps:

1. Construction of *Pseudomonas lemoignei* and *Bacillus stearothermophilus* 33M Genomic DNA Libraries and Methylase Selection Genomic DNA was prepared from *Pseudomonas lemoignei* and *Bacillus stearothermophilus* 33M and partially digested with restriction enzymes such as ApoI and Sau3AI. The digested genomic DNA was ligated to *E. coli* cloning/expression vectors such pUC19 or pBR322 with compatible ends. The ligated DNA was transformed into restriction minus *E. coli* competent cells such as RR1 and transformants were pooled and amplified. Plasmid DNA libraries were prepared and challenged with PleI or any isoschizomer. Following digestion, the plasmids were transformed back into RR1 cells. Survivors were screened for resistance to PleI digestion. The resistant clones were identified as methylase positive clones or plasmids that had simply lost the restriction sites. Sequencing the insert (skip to step 3) verified the cloning of a methylase gene.

2. PleI Endonuclease Activity Assays

PleI endonuclease activity assays were carried out using cells extracts of the M+ clones. No endonuclease activity was seen.

3. Sequencing of pleIM and the bstNBIIM Gene

The pleIM and the bstNBIIM genes were sequenced by primer walking. The pleIM gene is 852 bp, encoding a 283-aa protein with predicted molecular mass of 33.7 kDa. The bstNBIIM gene is 804 bp, encoding a 267-aa protein with a predicted molecular mass of 31.1 kDa.

4. Chromosome Walking via Inverse PCR to Isolate the PleI Endonuclease Gene

The *Pseudomonas lemoignei* genomic DNA was digested with 4 bp cutting restriction enzymes such as BfaI, NlaIII and Sau3AI. The digested DNA was ligated at a low DNA concentration and then used for inverse PCR amplification of the pleIR gene. Inverse PCR products were derived and sequenced. An ORF of 1668 bp was found downstream of the pleIM gene. This ORF is named pleIR gene. It encodes a 555-aa protein with predicted molecular mass of 64 kDa.

5. Cloning of BstNBIIM Gene into pSXY20 to Construct a Premodified Host

The bstNBIIM gene was amplified from the genomic DNA by PCR using two primers. The PCR DNA was digested with BamHI and SalI and ligated to pSYX20. The premodified host ER2502 [pSYX20-bstNBIIM] was used for expression of the mlyIR gene in *E. coli*.

6. Expression of pleIR Gene in Expression Vector pAGR3

The NcoI and XbaI sites were incorporated into the forward primer and reverse primers for cloning of the pleIR gene into the pAGR3 expression vector. The ribosome binding site, lac operator and Tac promoter of pAGR3 were utilized for pleIR gene expression.

The pleIR gene was amplified by PCR using a combination of Taq and Deep Vent DNA polymerase and primers. The PCR product was digested with NcoI and XbaI. and ligated to the pAGR3 expression vector. The ligated DNA was transformed into premodified host ER2502 [pSXY20-bstNBIIM]. Plasmids with the correct size insert were screened from the transformants. Cell extracts were prepared and assayed for PleI activity. Five out of six clones displayed high PleI activity (>100,000 U/g cells).

The present invention is further illustrated by the following Examples. These Examples are provided to aid in the understanding of the invention and are not construed as a limitation thereof.

The references cited above and below are herein incorporated by reference.

EXAMPLE 1

Cloning of pleI Restriction-modification System and BstNBII Modification System in E. coli 1. Preparation of Genomic DNA and Restriction Digestion of Genomic DNA Genomic DNA was prepared from *Pseudomonas lemoignei* and *Bacillus stearothermophilus* 33M (New England Biolabs collection #418 and 928 respectively) by the standard procedure consisting of the following steps:
(a) cell lysis by addition of lysozyme (2 mg/ml final), sucrose (1% final), and 50 mM Tris-HCl, pH 8.0
(b) cell lysis by addition of 10% SDS (final concentration 0.1%)
(c) cell lysis by addition of 1% Triton X-100 and 62 mM EDTA, 50 mM Tris-HCl, pH 8.0
(d) phenol-$CHCl_3$ extraction of DNA 3 times (equal volume) and $CHCl_3$ extraction once
(e) DNA dialysis in 4 liters of TE buffer, change 3 times
(f) RNA was removed by RNase A treatment and the genomic DNA was precipitated in 95% ethanol, spooled, washed, and resuspended in TE buffer.

Restriction enzymes ApoI, and Sau3AI were diluted by 2-fold serial dilutions. Five to ten $\mu$g genomic DNA was digested partially with ApoI and Sau3AI at 37° C. for one hour. The ApoI and Sau3AI partially digested genomic DNAs were respectively ligated to EcoRI or BamHI digested and CIP treated pUC19 in the case of PleI and LITMUS 28 in the case of BstNBII. The ligated DNA was used to transform *E. coli* RR1 competent cells by the standard procedure.

2. Construction of ApoI and Sau3AI Partial Genomic DNA Libraries and Selection of M.PleI and M.BstNBII by the Methylase Selection Method For the transformation experiments the antibiotic ampicillin was used for selection. These transformants were pooled and spun down. Plasmid DNA was prepared from the cells using the Qiagen Qiaprep spin plasmid kit. In the case of PleI, the plasmid libraries were challenged with PleI for 30 minutes at 37° C. followed by a 20 minute heat kill at 65° C. Following PleI digestion, the challenged DNAs were transformed back into RR1 competent cells. $Ap^R$ survivors were screened for resistance to PleI digestion. Resistant clones (M.PleI positive) were derived from the EcoRI partial libraries.

In the case of the *Bacillus stearothermophilus* 33M library the plasmid libraries were challenged with MlyI for 30 minutes at 37° C. followed by a 20 minute heat kill at 65° C. Following MlyI digestion, the challenged DNAs were transformed back into RR1 competent cells. $Ap^R$ survivors were screened for resistance to MlyI digestion. One resistant clone (M.BstNBII positive) was derived from the BamHI partial library.

3. Sequencing of pleIM and bstNBIIM Genes

The pleIM gene was sequenced using primer walking. The pleIM gene is 852 bp, encoding a 283-aa protein with predicted molecular mass of 33.7 kDa. Sequence comparison with other methylases in GenBank indicated that M.PleI is probably an N6-adenine methylase.

The bstNBIIM gene was sequenced using primer walking. The bstNBIIM gene is 804 bp, encoding a 267-aa protein with predicted molecular mass of 31.3 kDa. Sequence comparison with other methylases in GenBank indicated that M.BstNBII is probably an N6-adenine methylase.

4. Cloning of bstNBIIM Gene into pSXY20 to Construct a Premodified Host

Two primers were synthesized with the following sequence:
5' ATTGGATCCTAAGGAGGTGATCTAATG-GACACAGAAACTGCATCTG 3' (222-47) (SEQ ID NO:5)
5' TAAGTCGACTTATTCCCAAAATACCGGTTC G3' (222-42) (SEQ ID NO:6)

The bstNBIIM gene was amplified from the genomic DNA in PCR using primers 222-47 and 222-42 under PCR conditions of 95° C. 30 sec, 50° C. 1 min, 72° C. 1 min for 20 cycles. The PCR DNA was purified through a Qiagen spin column and digested with BamHI and SalI and ligated to pSYX20 with compatible ends. One clone was found to be resistant to MlyI digestion. The premodified host ER2502 [pSYX20-BstNBIIM] was used for expression of the pleIR gene in *E. coli*.

5. Cloning of pleIR Gene by Inverse PCR

A) Prepare genomic DNA—For the first round of inverse PCR, 1.5 $\mu$g of bacterial DNA was digested with 25 units of BfaI restriction endonuclease in 1×NEB Buffer 4 in a 50 $\mu$l reaction volume. The reaction was incubated at 37° C. for one hour, heat killed and looked at by running 13 $\mu$l on a 1% agarose gel. The digests were then circularized by incubating the remaining 37 $\mu$l (~1 $\mu$g) in 1×T4 DNA Ligase Buffer with 3000 units of T4 DNA Ligase in a 500 $\mu$l reaction volume at 16° C. overnight. A portion of this circular ligation reaction was then used as the template for subsequent inverse PCR reactions.

B) BfaI inverse PCR reaction—A set of inverse PCR primers were synthesized based on the DNA sequence of the pleIM gene.
5' CAAAGCATATAGTTGTTGCAAATTAT 3' (206-163) (SEQ ID NO:7)
5' CAACAGACTTAAATCTATTCCTTATA 3' (206-164) (SEQ ID NO:8)

Inverse PCR was carried out using primers 206-163 and 206-164 and the above mentioned DNA templates. A 490 bp product was observed. The product was gel purified and resuspended in 30 $\mu$l dH20. The PCR product was then sequenced using an ABI 373 automated sequencing system according to the manufacturer's instructions, using the PCR primers above as the sequencing primers. The BfaI inverse PCR product contained approximately 240 bp of new DNA sequence.

C) NlaIII inverse PCR reactions—Two inverse PCR primers complementary to newly read sequence from the BfaI PCR product were then synthesized, as below, and used in an inverse PCR reaction. Template preparation, inverse PCR, purification and DNA sequencing were performed as above but NlaIII was used to create the template as opposed to BfaI. A 550-bp PCR product was generated and sequenced. The sequence contained approximately 463-bp of new DNA sequence.

5' CTTTGATGGTGAAGGTAAGAATGA 3' (209-143) (SEQ ID NO:9)

5' AAACTTTCTTCTTTAAGAATTTTC 3' (209-144) (SEQ ID NO:10)

D) Sau3AI inverse PCR reactions—Two inverse PCR primers complementary to newly read sequence from the NlaIII PCR product were then synthesized, as below, and used in an inverse PCR reaction. Template preparation, inverse PCR, purification and DNA sequencing were performed as above but Sau3AI was used to create the template as opposed to NlaIII. A 1685-bp PCR product was generated and sequenced. The sequence revealed the complete open reading frame of the pleIR gene.

5' AAATTTCAGCTGCCATCTCCATA 3' (211-168) (SEQ ID NO:11)

5' AAGCATTTGCCTCAAAAATATATC 3' (211-169) (SEQ ID NO:12)

6. Expression of pleIR Gene in Expression Vector pAGR3

Two restriction sites (NcoI site and XbaI site) were incorporated into the forward and reverse primers, respectively for cloning of pleIR gene into the pAGR3 expression vector. Two primers were synthesized to amplify the pleIR gene by PCR. The primers had the following sequence:

5' AAACAGACCATGGCAAAGCCTATTGAT-AGTAAAGTT 3' (236-126) (SEQ ID NO:13)

5' AATCTTAAGTCTAGATTATCATAAC-CCAATCATATGAAAAATATT 3' (234-198) (SEQ ID NO:14)

The pleIR gene was amplified by PCR using a combination of Taq and Deep Vent® DNA polymerase and primers 236-126 and 234-198 under conditions of 940° C. 30 sec, 550° C. 1 min, 720° C. 2 min for 25 cycles. The PCR product was purified by Qiagen spin column and both the PCR product and vector pAGR3 were digested with NcoI and XbaI. The digested vector and PCR product were run on a 1% low melting point NuSieve agarose gel in TAE buffer. The DNA bands were cut out of the gel, and treated with β-Agarase and ethanol precipitated. The PCR DNA was then ligated to the prepared pAGR3. The ligated DNA was transformed into premodified host ER2502 [pSXY20-bstNBIIM] and $Ap^R$ $Kan^R$ transformants were selected for.

Among 6 plasmid mini-preparation, 6 clones carried the desired insert. Five of the six expressed PleI activity.

One of these clones with plasmid constructs pAGR3-pleIR and pSXY20-bstNBIIM was selected for producing the PleI endonuclease. The *E. coli* strain which contains both pAGR3-pleIR and pSXY20-bstNBIIM was designated as NEB #1291. The yield of recombinant PleI in strain NEB #1291 was approximately 100,000 units/gram of cells.

pAGR3 containing PleI restriction endonuclease gene from *Pseudomonas lemoignei* in *E. coli* ER2566 has been deposited under the terms and conditions of the Budapest Treaty with the American Type Culture Collection on Mar. 15, 2001 and received ATCC Accession No. PTA-3184.

What is claimed is:

1. Isolated DNA coding for the PleI restriction endonuclease wherein the isolated DNA is obtainable from *Pseudomonas lemoignei*.

2. A recombinant DNA vector comprising a vector into which a DNA segment coding for the PleI restriction endonuclease as been inserted.

3. A host cell transformed by the vector of claim 2.

4. A method of producing a PleI restriction endonuclease comprising culturing a host cell transformed with the vector of claim 2 under conditions suitable for expression of said endonuclease.

5. The host cell of claim 3 comprising ATCC Accession No. PTA-3184.

* * * * *

UNITED STATES PATENT AND TRADEMARK OFFICE
CERTIFICATE OF CORRECTION

PATENT NO.   : 6,391,608 B1
DATED        : May 21, 2002
INVENTOR(S)  : Kong et al.

It is certified that error appears in the above-identified patent and that said Letters Patent is hereby corrected as shown below:

Column 1,
Line 4, replace "*E. COLI*" with -- *E. COLI* --
Line 23, replace "(M.BstNBI)" with -- (M.BstNBII) --

Column 2,
Line 63, replace "U.S. Pat. No. 5,498,525" with -- U.S. Pat. No. 5,498,535 --

Column 3,
Line 48, replace "pleIr" with -- pleIR --
Line 59, replace "pSXY20" with -- pSYX20 --

Column 4,
Line 54, replace "pSXY20" with -- pSYX20 --

Column 5,
Line 2, replace "Vent" with -- Vent® --
Line 3, replace "XbaI." with -- XbaI --

Column 6,
Line 56, replace "dH20" with -- dH$_c$0 --

Column 8,
Line 6, replace "940ºC" with -- 94ºC --
Line 7, replace "550ºC. 1 min. 720ºC" with -- 55ºC 1 min, 72ºC --
Lines 15, 19 and 21, replace "pSXY20" with -- pSYX20 --

Signed and Sealed this

Twenty-ninth Day of April, 2003

JAMES E. ROGAN
*Director of the United States Patent and Trademark Office*

SEQUENCE LISTING

<160> NUMBER OF SEQ ID NOS: 14

<210> SEQ ID NO 1
<211> LENGTH: 852
<212> TYPE: DNA
<213> ORGANISM: Pseudomonas lemoignei
<220> FEATURE:
<221> NAME/KEY: CDS
<222> LOCATION: (1)..(849)

<400> SEQUENCE: 1

```
atg aag cca tta gtt aaa tat aga ggt gga a ag tct aag gaa att cca        48
Met Lys Pro Leu Val Lys Tyr Arg Gly Gly L ys Ser Lys Glu Ile Pro
 1               5                  10                  15 tat cta att aaa cat atc cct gaa ttt aaa g gg cgc tac ata gag cct        96
Tyr Leu Ile Lys His Ile Pro Glu Phe Lys G ly Arg Tyr Ile Glu Pro
            20                  25                  30 ttt ttt ggt ggg ggg gct tta ttt ttt tat a ta gag cca gaa aaa tct       144
Phe Phe Gly Gly Gly Ala Leu Phe Phe Tyr I le Glu Pro Glu Lys Ser
        35                  40                  45 att atc aat gac att aat aaa aaa ctt ata g at ttt tat cga gat gtt       192
Ile Ile Asn Asp Ile Asn Lys Lys Leu Ile A sp Phe Tyr Arg Asp Val
    50                  55                  60 aaa gat aac ttt gtt caa ttg cgt cat gag c tt gat gag ata gaa tgt       240
Lys Asp Asn Phe Val Gln Leu Arg His Glu L eu Asp Glu Ile Glu Cys
 65                  70                  75                  80 att tat gaa aag aat aga gtt gaa tac gaa a ct aga aag aaa tta aat       288
Ile Tyr Glu Lys Asn Arg Val Glu Tyr Glu T hr Arg Lys Lys Leu Asn
                85                  90                  95 cct act gaa cgt gta gat gat gga aat gaa g at ttc tat tac ttc atg       336
Pro Thr Glu Arg Val Asp Asp Gly Asn Glu A sp Phe Tyr Tyr Phe Met
            100                 105                 110
```

-continued

```
agg aat gaa ttc aat aaa gat ttt tcg gat a ga tat ctt tca tca aca      384
Arg Asn Glu Phe Asn Lys Asp Phe Ser Asp A rg Tyr Leu Ser Ser Thr
        115                 120                 125 ctg tat ttt tat ata aat aag act gcg tac t ct gga atg att aga tat      432
Leu Tyr Phe Tyr Ile Asn Lys Thr Ala Tyr S er Gly Met Ile Arg Tyr
130                 135                 140 aac tca aaa ggt gag ttt aat gtt ccg ttt g gt aga tat aaa aat ctc      480
Asn Ser Lys Gly Glu Phe Asn Val Pro Phe G ly Arg Tyr Lys Asn Leu
145                 150                 155                 160 aat aca aaa ctt gtg gct aat gaa cat cac t tg tta atg cag ggt gct      528
Asn Thr Lys Leu Val Ala Asn Glu His His L eu Leu Met Gln Gly Ala
            165                 170                 175 cag ata ttt aat gaa gat tac agc gag atc t tc aag atg gcg aga aaa      576
Gln Ile Phe Asn Glu Asp Tyr Ser Glu Ile P he Lys Met Ala Arg Lys
        180                 185                 190 gat gat ttt ata ttt cta gac cct ccc tat g at tgc gta ttt agt gat      624
Asp Asp Phe Ile Phe Leu Asp Pro Pro Tyr A sp Cys Val Phe Ser Asp
            195                 200                 205 tat ggt aat gag gaa tat aaa gat ggt ttc a at gta gat gct cat gtg      672
Tyr Gly Asn Glu Glu Tyr Lys Asp Gly Phe A sn Val Asp Ala His Val
210                 215                 220 aaa ttg agt gag gac ttt aag aaa ttg aaa t gc aaa gcc atg atg gtt      720
Lys Leu Ser Glu Asp Phe Lys Lys Leu Lys C ys Lys Ala Met Met Val
225                 230                 235                 240 atc ggt aag act gaa ttg act gat ggg ttg t at aag aaa atg att att      768
Ile Gly Lys Thr Glu Leu Thr Asp Gly Leu T yr Lys Lys Met Ile Ile
            245                 250                 255 gat gaa tac gat aaa agt tat tct gtg aat a ta agg aat aga ttt aag      816
Asp Glu Tyr Asp Lys Ser Tyr Ser Val Asn I le Arg Asn Arg Phe Lys
        260                 265                 270 tct gtt gca aag cat ata gtt gtt gca aat t at tga                      852
Ser Val Ala Lys His Ile Val Val Ala Asn T yr
        275                 280
```

<210> SEQ ID NO 2
<211> LENGTH: 283
<212> TYPE: PRT
<213> ORGANISM: Pseudomonas lemoignei

<400> SEQUENCE: 2

```
Met Lys Pro Leu Val Lys Tyr Arg Gly Gly L ys Ser Lys Glu Ile Pro
 1               5                  10                  15

Tyr Leu Ile Lys His Ile Pro Glu Phe Lys G ly Arg Tyr Ile Glu Pro
                20                  25                  30

Phe Phe Gly Gly Gly Ala Leu Phe Phe Tyr I le Glu Pro Glu Lys Ser
            35                  40                  45

Ile Ile Asn Asp Ile Asn Lys Lys Leu Ile A sp Phe Tyr Arg Asp Val
        50                  55                  60

Lys Asp Asn Phe Val Gln Leu Arg His Glu L eu Asp Glu Ile Glu Cys
 65                  70                  75                  80

Ile Tyr Glu Lys Asn Arg Val Glu Tyr Glu T hr Arg Lys Lys Leu Asn
                85                  90                  95

Pro Thr Glu Arg Val Asp Asp Gly Asn Glu A sp Phe Tyr Tyr Phe Met
            100                 105                 110

Arg Asn Glu Phe Asn Lys Asp Phe Ser Asp A rg Tyr Leu Ser Ser Thr
        115                 120                 125

Leu Tyr Phe Tyr Ile Asn Lys Thr Ala Tyr S er Gly Met Ile Arg Tyr
130                 135                 140
```

```
Asn Ser Lys Gly Glu Phe Asn Val Pro Phe G ly Arg Tyr Lys Asn Leu
145                 150                 155                 160

Asn Thr Lys Leu Val Ala Asn Glu His His L eu Leu Met Gln Gly Ala
            165                 170                 175

Gln Ile Phe Asn Glu Asp Tyr Ser Glu Ile P he Lys Met Ala Arg Lys
            180                 185                 190

Asp Asp Phe Ile Phe Leu Asp Pro Pro Tyr A sp Cys Val Phe Ser Asp
            195                 200                 205

Tyr Gly Asn Glu Glu Tyr Lys Asp Gly Phe A sn Val Asp Ala His Val
            210                 215                 220

Lys Leu Ser Glu Asp Phe Lys Lys Leu Lys C ys Lys Ala Met Met Val
225                 230                 235                 240

Ile Gly Lys Thr Glu Leu Thr Asp Gly Leu T yr Lys Lys Met Ile Ile
            245                 250                 255

Asp Glu Tyr Asp Lys Ser Tyr Ser Val Asn I le Arg Asn Arg Phe Lys
            260                 265                 270

Ser Val Ala Lys His Ile Val Val Ala Asn T yr
            275                 280

<210> SEQ ID NO 3
<211> LENGTH: 1668
<212> TYPE: DNA
<213> ORGANISM: Pseudomonas lemoignei
<220> FEATURE:
<221> NAME/KEY: CDS
<222> LOCATION: (1)..(1668)

<400> SEQUENCE: 3 atg gca aag cct att gat agt aaa gtt cta t tt att act acg tca cca      48
Met Ala Lys Pro Ile Asp Ser Lys Val Leu P he Ile Thr Thr Ser Pro
 1               5                  10                  15 cga acg cct gaa aag atg gtt cct gag ata g ag ctt tta gat aag aat      96
Arg Thr Pro Glu Lys Met Val Pro Glu Ile G lu Leu Leu Asp Lys Asn
            20                  25                  30 ttt aat ggg gat gtt tgg aat aaa gat acc c aa act gca ttc atg aaa     144
Phe Asn Gly Asp Val Trp Asn Lys Asp Thr G ln Thr Ala Phe Met Lys
        35                  40                  45 att ctt aaa gaa gaa agt ttc ttt gat ggt g aa ggt aag aat gat cct     192
Ile Leu Lys Glu Glu Ser Phe Phe Asp Gly G lu Gly Lys Asn Asp Pro
    50                  55                  60 gca ttt agt gct aga gat aga ata aat aga g cg cca aaa tca cta ggt     240
Ala Phe Ser Ala Arg Asp Arg Ile Asn Arg A la Pro Lys Ser Leu Gly
65                  70                  75                  80 ttt gtc att ttg aca cct aaa tta tct tta a ct gat gct ggt gtt gag     288
Phe Val Ile Leu Thr Pro Lys Leu Ser Leu T hr Asp Ala Gly Val Glu
                85                  90                  95 tta att aaa gca aaa aga aaa gat gat ata t tt ttg agg caa atg ctt     336
Leu Ile Lys Ala Lys Arg Lys Asp Asp Ile P he Leu Arg Gln Met Leu
            100                 105                 110 aaa ttt cag ctg cca tct cca tac cat aag t ta tca gat aag gca gca     384
Lys Phe Gln Leu Pro Ser Pro Tyr His Lys L eu Ser Asp Lys Ala Ala
        115                 120                 125 ctt ttt tat gta aaa cct tat ctt gaa ata t tt aga ttg gtt cgt cat     432
Leu Phe Tyr Val Lys Pro Tyr Leu Glu Ile P he Arg Leu Val Arg His
    130                 135                 140 ttt ggt tct ttg acc ttt gat gag tta atg a tt ttt ggt ttg caa att     480
Phe Gly Ser Leu Thr Phe Asp Glu Leu Met I le Phe Gly Leu Gln Ile
145                 150                 155                 160 ata gat ttt aga att ttt aat caa att gtt g at aaa att gaa gat ttt     528
```

```
Ile Asp Phe Arg Ile Phe Asn Gln Ile Val Asp Lys Ile Glu Asp Phe
            165                 170                 175 aga gtg ggt aag att gaa aat aaa ggt agg tat aaa act tat aaa aaa    576
Arg Val Gly Lys Ile Glu Asn Lys Gly Arg Tyr Lys Thr Tyr Lys Lys
        180                 185                 190 gag cgg ttt gag gaa gag ctt ggg aaa ata tat aaa gat gag ttg ttt    624
Glu Arg Phe Glu Glu Glu Leu Gly Lys Ile Tyr Lys Asp Glu Leu Phe
        195                 200                 205 ggt tta aca gag gct tcg gct aaa acg tta att acc aaa aaa ggt aac    672
Gly Leu Thr Glu Ala Ser Ala Lys Thr Leu Ile Thr Lys Lys Gly Asn
        210                 215                 220 aat atg agg gac tat gct gat gca tgc gtt aga tat ttg cgt gcg aca    720
Asn Met Arg Asp Tyr Ala Asp Ala Cys Val Arg Tyr Leu Arg Ala Thr
225                 230                 235                 240 ggg atg gtt aat gtt tct tat caa ggg aaa tct ctc tca att gtt caa    768
Gly Met Val Asn Val Ser Tyr Gln Gly Lys Ser Leu Ser Ile Val Gln
                245                 250                 255 gag aaa aaa gaa gaa gtt gat ttc ttt tta aag aat act gag aga gaa    816
Glu Lys Lys Glu Glu Val Asp Phe Phe Leu Lys Asn Thr Glu Arg Glu
            260                 265                 270 cct tgc ttt ata aat gat gaa gca tca tat gtg agt tat ctt ggt aat    864
Pro Cys Phe Ile Asn Asp Glu Ala Ser Tyr Val Ser Tyr Leu Gly Asn
        275                 280                 285 cct aat tac ccc aaa ctt ttt gtt gat gac gta gat agg att aaa aag    912
Pro Asn Tyr Pro Lys Leu Phe Val Asp Asp Val Asp Arg Ile Lys Lys
        290                 295                 300 aaa ctt cga ttt gat ttt aag aag act aat aaa gtt aat gcc ttg aca    960
Lys Leu Arg Phe Asp Phe Lys Lys Thr Asn Lys Val Asn Ala Leu Thr
305                 310                 315                 320 ctt cct gag ttg aaa gag gag tta gag aat gaa att cta agt aga aaa   1008
Leu Pro Glu Leu Lys Glu Glu Leu Glu Asn Glu Ile Leu Ser Arg Lys
                325                 330                 335 gag aat ata tta aaa agt caa ata tct gat att aaa aac ttt aag tta   1056
Glu Asn Ile Leu Lys Ser Gln Ile Ser Asp Ile Lys Asn Phe Lys Leu
            340                 345                 350 tac gaa gac att caa gag gtt ttt gag aag ata gaa aat gat aga aca   1104
Tyr Glu Asp Ile Gln Glu Val Phe Glu Lys Ile Glu Asn Asp Arg Thr
        355                 360                 365 cta tct gat gct cca ttg atg ctt gaa tgg aat aca tgg cgt gca atg   1152
Leu Ser Asp Ala Pro Leu Met Leu Glu Trp Asn Thr Trp Arg Ala Met
        370                 375                 380 act atg ctg gat ggt ggt gaa atc aaa gca aat ttg aaa ttt gat gat   1200
Thr Met Leu Asp Gly Gly Glu Ile Lys Ala Asn Leu Lys Phe Asp Asp
385                 390                 395                 400 ttt gga agt cca atg tct acg gct att gga aat atg cca gat ata gtg   1248
Phe Gly Ser Pro Met Ser Thr Ala Ile Gly Asn Met Pro Asp Ile Val
                405                 410                 415 tgt gaa tat gat gac ttc cag ttg tct gta gaa gtc aca atg gca agc   1296
Cys Glu Tyr Asp Asp Phe Gln Leu Ser Val Glu Val Thr Met Ala Ser
            420                 425                 430 ggg caa aag caa tat gaa atg gaa ggt gag cca gtc tcg cgg cac tta   1344
Gly Gln Lys Gln Tyr Glu Met Glu Gly Glu Pro Val Ser Arg His Leu
        435                 440                 445 ggt aaa cta aag aaa agt tct gaa aaa cca gta tat tgt tta ttc att   1392
Gly Lys Leu Lys Lys Ser Ser Glu Lys Pro Val Tyr Cys Leu Phe Ile
        450                 455                 460 gct cct aaa att aat cca tcc tca gta gca cac ttc ttt atg tct cat   1440
Ala Pro Lys Ile Asn Pro Ser Ser Val Ala His Phe Phe Met Ser His
465                 470                 475                 480
```

-continued

```
aaa gtg gat att gaa tat tat ggt ggg aaa a gc cta att att cct ttg    1488
Lys Val Asp Ile Glu Tyr Tyr Gly Gly Lys S er Leu Ile Ile Pro Leu
            485                 490                 495 gag tta agt gtt ttt agg aag atg att gag g at act ttt aaa gca tcg    1536
Glu Leu Ser Val Phe Arg Lys Met Ile Glu A sp Thr Phe Lys Ala Ser
        500                 505                 510 tat ata cca aaa tct gat aat gtt cat aaa t ta ttt aag aat ttt gct    1584
Tyr Ile Pro Lys Ser Asp Asn Val His Lys L eu Phe Lys Asn Phe Ala
        515                 520                 525 tca att gca gat gag gca ggt aat gag aaa g tt tgg tat gaa ggt gta    1632
Ser Ile Ala Asp Glu Ala Gly Asn Glu Lys V al Trp Tyr Glu Gly Val
        530                 535                 540 aaa aga act gca atg aat tgg ctt tct tta a gc taa                     1668
Lys Arg Thr Ala Met Asn Trp Leu Ser Leu S er
545                 550                 555
```

<210> SEQ ID NO 4
<211> LENGTH: 555
<212> TYPE: PRT
<213> ORGANISM: Pseudomonas lemoignei

<400> SEQUENCE: 4

```
Met Ala Lys Pro Ile Asp Ser Lys Val Leu P he Ile Thr Thr Ser Pro
1               5                   10                  15

Arg Thr Pro Glu Lys Met Val Pro Glu Ile G lu Leu Leu Asp Lys Asn
            20                  25                  30

Phe Asn Gly Asp Val Trp Asn Lys Asp Thr G ln Thr Ala Phe Met Lys
        35                  40                  45

Ile Leu Lys Glu Glu Ser Phe Phe Asp Gly G lu Gly Lys Asn Asp Pro
    50                  55                  60

Ala Phe Ser Ala Arg Asp Arg Ile Asn Arg A la Pro Lys Ser Leu Gly
65                  70                  75                  80

Phe Val Ile Leu Thr Pro Lys Leu Ser Leu T hr Asp Ala Gly Val Glu
                85                  90                  95

Leu Ile Lys Ala Lys Arg Lys Asp Asp Ile P he Leu Arg Gln Met Leu
            100                 105                 110

Lys Phe Gln Leu Pro Ser Pro Tyr His Lys L eu Ser Asp Lys Ala Ala
        115                 120                 125

Leu Phe Tyr Val Lys Pro Tyr Leu Glu Ile P he Arg Leu Val Arg His
    130                 135                 140

Phe Gly Ser Leu Thr Phe Asp Glu Leu Met I le Phe Gly Leu Gln Ile
145                 150                 155                 160

Ile Asp Phe Arg Ile Phe Asn Gln Ile Val A sp Lys Ile Glu Asp Phe
                165                 170                 175

Arg Val Gly Lys Ile Glu Asn Lys Gly Arg T yr Lys Thr Tyr Lys Lys
            180                 185                 190

Glu Arg Phe Glu Glu Leu Gly Lys Ile T yr Lys Asp Glu Leu Phe
        195                 200                 205

Gly Leu Thr Glu Ala Ser Ala Lys Thr Leu I le Thr Lys Lys Gly Asn
    210                 215                 220

Asn Met Arg Asp Tyr Ala Asp Ala Cys Val A rg Tyr Leu Arg Ala Thr
225                 230                 235                 240

Gly Met Val Asn Val Ser Tyr Gln Gly Lys S er Leu Ser Ile Val Gln
                245                 250                 255

Glu Lys Lys Glu Glu Val Asp Phe Phe Leu L ys Asn Thr Glu Arg Glu
            260                 265                 270
```

```
Pro Cys Phe Ile Asn Asp Glu Ala Ser Tyr Val Ser Tyr Leu Gly Asn
        275                 280                 285

Pro Asn Tyr Pro Lys Leu Phe Val Asp Val Asp Arg Ile Lys Lys
    290                 295                 300

Lys Leu Arg Phe Asp Phe Lys Lys Thr Asn Lys Val Asn Ala Leu Thr
305                 310                 315                 320

Leu Pro Glu Leu Lys Glu Leu Glu Asn Glu Ile Leu Ser Arg Lys
                325                 330                 335

Glu Asn Ile Leu Lys Ser Gln Ile Ser Asp Ile Lys Asn Phe Lys Leu
                340                 345                 350

Tyr Glu Asp Ile Gln Glu Val Phe Glu Lys Ile Glu Asn Asp Arg Thr
                355                 360                 365

Leu Ser Asp Ala Pro Leu Met Leu Glu Trp Asn Thr Trp Arg Ala Met
                370                 375                 380

Thr Met Leu Asp Gly Gly Glu Ile Lys Ala Asn Leu Lys Phe Asp Asp
385                 390                 395                 400

Phe Gly Ser Pro Met Ser Thr Ala Ile Gly Asn Met Pro Asp Ile Val
                405                 410                 415

Cys Glu Tyr Asp Asp Phe Gln Leu Ser Val Glu Val Thr Met Ala Ser
                420                 425                 430

Gly Gln Lys Gln Tyr Glu Met Glu Gly Glu Pro Val Ser Arg His Leu
                435                 440                 445

Gly Lys Leu Lys Lys Ser Ser Glu Lys Pro Val Tyr Cys Leu Phe Ile
450                 455                 460

Ala Pro Lys Ile Asn Pro Ser Val Ala His Phe Phe Met Ser His
465                 470                 475                 480

Lys Val Asp Ile Glu Tyr Tyr Gly Gly Lys Ser Leu Ile Ile Pro Leu
                485                 490                 495

Glu Leu Ser Val Phe Arg Lys Met Ile Glu Asp Thr Phe Lys Ala Ser
                500                 505                 510

Tyr Ile Pro Lys Ser Asp Asn Val His Lys Leu Phe Lys Asn Phe Ala
                515                 520                 525

Ser Ile Ala Asp Glu Ala Gly Asn Glu Lys Val Trp Tyr Glu Gly Val
                530                 535                 540

Lys Arg Thr Ala Met Asn Trp Leu Ser Leu Ser
545                 550                 555

<210> SEQ ID NO 5
<211> LENGTH: 46
<212> TYPE: DNA
<213> ORGANISM: Bacillus stearothermophilus

<400> SEQUENCE: 5
attggatcct aaggaggtga tctaatggac acagaaactg catctg         46

<210> SEQ ID NO 6
<211> LENGTH: 30
<212> TYPE: DNA
<213> ORGANISM: Bacillus stearothermophilus

<400> SEQUENCE: 6
taagtcgact tattcccaaa ataccggttc         30

<210> SEQ ID NO 7
<211> LENGTH: 26
<212> TYPE: DNA
<213> ORGANISM: Pseudomonas lemoignei
```

-continued

```
<400> SEQUENCE: 7
caaagcatat agttgttgca aattat                                    26

<210> SEQ ID NO 8
<211> LENGTH: 26
<212> TYPE: DNA
<213> ORGANISM: Pseudomonas lemoignei

<400> SEQUENCE: 8
caacagactt aaatctattc cttata                                    26

<210> SEQ ID NO 9
<211> LENGTH: 24
<212> TYPE: DNA
<213> ORGANISM: Pseudomonas lemoignei

<400> SEQUENCE: 9
ctttgatggt gaaggtaaga atga                                      24

<210> SEQ ID NO 10
<211> LENGTH: 24
<212> TYPE: DNA
<213> ORGANISM: Pseudomonas lemoignei

<400> SEQUENCE: 10
aaactttctt ctttaagaat tttc                                      24

<210> SEQ ID NO 11
<211> LENGTH: 23
<212> TYPE: DNA
<213> ORGANISM: Pseudomonas lemoignei

<400> SEQUENCE: 11
aaatttcagc tgccatctcc ata                                       23

<210> SEQ ID NO 12
<211> LENGTH: 24
<212> TYPE: DNA
<213> ORGANISM: Pseudomonas lemoignei

<400> SEQUENCE: 12
aagcatttgc ctcaaaaata tatc                                      24

<210> SEQ ID NO 13
<211> LENGTH: 36
<212> TYPE: DNA
<213> ORGANISM: Pseudomonas lemoignei

<400> SEQUENCE: 13
aaacagacca tggcaaagcc tattgatagt aaagtt                         36

<210> SEQ ID NO 14
<211> LENGTH: 45
<212> TYPE: DNA
<213> ORGANISM: Pseudomonas lemoignei

<400> SEQUENCE: 14
aatcttaagt ctagattatc ataacccaat catatgaaaa atatt               45
```